(12) United States Patent
Kitsos

(10) Patent No.: US 12,390,404 B2
(45) Date of Patent: Aug. 19, 2025

(54) DEVICE AND METHOD FOR PROVIDING CUSTOMIZED SKIN COLOR MATCHING SUNSCREEN

(71) Applicant: Kristina Kitsos, Los Angeles, CA (US)

(72) Inventor: Kristina Kitsos, Los Angeles, CA (US)

( * ) Notice: Subject to any disclaimer, the term of this patent is extended or adjusted under 35 U.S.C. 154(b) by 11 days.

(21) Appl. No.: 18/474,923

(22) Filed: Sep. 26, 2023

(65) Prior Publication Data

US 2024/0024212 A1  Jan. 25, 2024

Related U.S. Application Data

(63) Continuation of application No. 17/175,531, filed on Feb. 12, 2021, now Pat. No. 11,992,542.

(60) Provisional application No. 62/948,141, filed on Dec. 13, 2019.

(51) Int. Cl.
| | |
|---|---|
| *A61K 8/29* | (2006.01) |
| *A61K 8/03* | (2006.01) |
| *A61K 8/27* | (2006.01) |
| *A61Q 1/02* | (2006.01) |
| *A61Q 17/04* | (2006.01) |

(52) U.S. Cl.
CPC .................. *A61K 8/29* (2013.01); *A61K 8/03* (2013.01); *A61K 8/27* (2013.01); *A61Q 1/02* (2013.01); *A61Q 17/04* (2013.01); *A61K 2800/43* (2013.01); *A61K 2800/52* (2013.01); *A61K 2800/805* (2013.01); *A61K 2800/87* (2013.01); *A61K 2800/882* (2013.01)

(58) Field of Classification Search
None
See application file for complete search history.

(56) References Cited

U.S. PATENT DOCUMENTS

| | | |
|---|---|---|
| 6,214,322 B1 | 4/2001 | Castro et al. |
| 2017/0228892 A1* | 8/2017 | Nichol ................. G06T 7/90 |

OTHER PUBLICATIONS

Final Office Action dated Oct. 13, 2023, in connection with U.S. Appl. No. 17/175,531, 7 pages.

* cited by examiner

*Primary Examiner* — Nannette Holloman

(57) ABSTRACT

Disclosed is a method for providing customized skin color matching sunscreen for a user. The method includes adding one or more basic sunscreen compounds, wherein the one or more sunscreen compounds includes at least one sun blocking active agent, adding a pigmented solution to the one or more basic sunscreen compounds, wherein the pigmented solution includes one or more pigments, determining a first amount of the one or more basic sunscreen compounds and a second amount of the pigmented solution for mixing, wherein the determining the first amount and the second amount is performed based on at least a skin tone of the user, and mechanically mixing the first amount and the second amount.

20 Claims, 4 Drawing Sheets

DEVICE AND METHOD FOR PROVIDING CUSTOMIZED SKIN COLOR MATCHING SUNSCREEN

CROSS-REFERENCE TO RELATED APPLICATION(S) AND CLAIM OF PRIORITY

This application is a continuation of U.S. patent application Ser. No. 17/175,531, filed on Feb. 12, 2021, which claims priority to: U.S. Provisional Patent Application No. 62/948,141, filed on Dec. 13, 2019. The above-identified provisional patent application is hereby incorporated by reference in its entirety.

TECHNICAL FIELD

This relates generally to a device and method for applying sunscreen, and more specifically to a device and method for providing customized skin color matching sunscreen.

BACKGROUND

Ultraviolet rays are known to cause premature aging of the skin, skin cancer and other ailments such as sun burn. Currently, various products for protection against sunscreen (i.e., sun-blocks or sunscreens) are available in the form of lotions for applying to the skin in order to block harmful rays from the sun. A sun-block product may contain organic chemicals (e.g., Oxybenzone) or mineral compounds (e.g., oxidized zinc or titanium) known for their property to absorb harmful rays. Existence of such chemicals or mineral compounds is to prevent the rays from causing damage to living cells.

One of the most effective known sunscreens is zinc oxide-based sunscreen, provided that it contains a sufficient concentration of zinc oxide. An effective zinc oxide-based sunscreen usually contains between 10% and 20% of zinc oxide. A drawback of zinc oxide-based sunscreens is that a layer of white-color lotion remains on the skin and appears chalky on the skin. The latter feature makes zinc oxide-based sunscreens cosmetically unappealing, which discourages their use by consumers. Therefore, there is a need for a sunscreen product that combines a mineral-based sunscreen for skin protection while mitigating the cosmetic drawbacks of such a product.

SUMMARY

In some embodiments, a method for providing customized skin color matching sunscreen for a user is disclosed. The method includes adding one or more basic sunscreen compounds, wherein the one or more sunscreen compounds includes at least one sun blocking active agent, adding a pigmented solution to the one or more basic sunscreen compounds, wherein the pigmented solution includes one or more pigments, determining a first amount of the one or more basic sunscreen compounds and a second amount of the pigmented solution for mixing, wherein the determining the first amount and the second amount is performed based on at least a skin tone of the user, and mechanically mixing the first amount and the second amount.

In some embodiments, a system for providing customized skin color matching sunscreen for a user is disclosed. The system includes a reservoir including a first chamber, the first chamber configured to store one or more basic sunscreen compounds, and a second chamber, the second chamber configured to store one or more pigmented solutions, wherein the first chamber and the second chamber are separate from each other, and a delivery device located above the reservoir, the delivery device configured to pull the one or more basic sunscreen compounds from the first chamber via a first tube, and to pull the one or more pigmented solutions from the second chamber via a second tube, the delivery device including a dial, the dial configured to allow selecting a first amount of the one or more basic sunscreen compounds from the first chamber and a second amount of the one or more pigmented solutions to be pulled by the delivery device from the second chamber, wherein the first amount and the second amount are determined based at least in part on a skin tone of the user, and a nozzle configured to transfer the pulled first amount of the one or more basic sunscreen compounds and second amount of the one or more pigmented solutions to the user.

In some embodiments, a system for providing customized skin color matching sunscreen for a user is disclosed. The system includes a reservoir including a first chamber, the first chamber configured to store one or more mineral-based sunscreen compounds, and a second chamber, the second chamber configured to store one or more creams having dark pigments, wherein the first chamber and the second chamber are separate from each other, a first delivery device located on a first upper side of the reservoir, the first delivery device configured to pull the one or more mineral-based sunscreen compounds from the first chamber via a first pump and through a first tube, the first delivery device including a first nozzle configured to transfer the pulled one or more mineral-based sunscreen compounds to the user, and a second delivery device located on a second upper side the reservoir, the second delivery device configured to pull the one or more creams having dark pigments from the second chamber via a second pump and through a second tube, the second delivery device includes a second nozzle configured to transfer the pulled one or more creams having dark pigments to the user.

BRIEF DESCRIPTION OF THE DRAWINGS

So that the present disclosure can be understood by those of ordinary skill in the art, a more detailed description can be had by reference to aspects of some illustrative embodiments, some of which are shown in the accompanying drawings.

Figure 1:
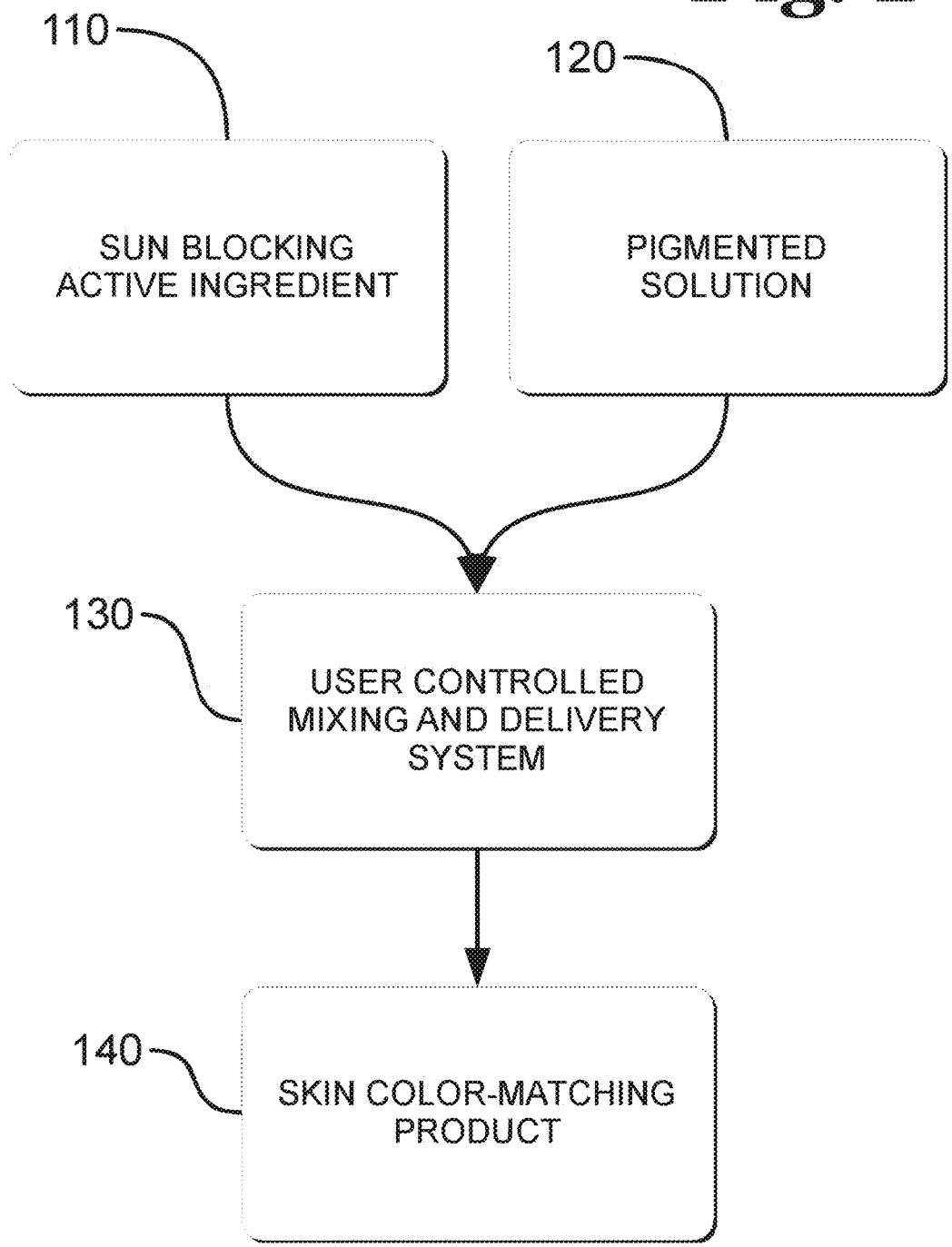
FIG. 1 is a simplified block diagram of a method for providing customized skin color matching sunscreen, in accordance with some embodiments.

In accordance with common practice some features illustrated in the drawings cannot be drawn to scale. Accordingly, the dimensions of some features can be arbitrarily expanded or reduced for clarity. In addition, some of the drawings cannot depict all the components of a given system, method or device. Finally, like reference numerals can be used to denote like features throughout the specification and figures.

DETAILED DESCRIPTION

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are only used to distinguish one element from another. For example, a first contact could be termed a second contact, and, similarly, a second contact could be termed a first contact, without departing from the scope of the various described embodiments. The first contact and the second contact are both contacts, but they are not the same contact, unless the context clearly indicates otherwise.

The terminology used in the description of the various described embodiments herein is for the purpose of describing particular embodiments only and is not intended to be limiting. As used in the description of the various described embodiments and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including", "comprises", and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

It should be appreciated that in the development of any actual implementation (as in any development project), numerous decisions must be made to achieve the invention's specific goals (e.g., compliance with system and business-related constraints), and that these goals will vary from one implementation to another. It will also be appreciated that such development efforts might be complex and time consuming but would nevertheless be a routine undertaking for those of ordinary skill in the art of image capture having the benefit of this disclosure.

Throughout the disclosure, a "final product" refers to a sunscreen that has been produced using the teaching of the invention. The latter, at times, is simply referred to as a sunscreen. Where emphasis is made that the sunscreen of concern is a sunscreen product that is made available to the invention in order to produce a personalized product, the term "basic" is used to make such emphasis. In the absence of such emphasis, though, it will be apparent from the context of the description to which product the reference is made.

A "pigmented product" refers to any substance that is available for human use as a cosmetic. The latter includes any colored substance available for use in cosmetic products such as make up products.

A "delivery device" of the sunscreen product according to the invention includes any device capable of moving fluids or viscous products from one or more chambers of a container and delivering the products under the control of a user for a custom application. Such device may include mechanical components, manually or electrically powered pumping systems or any other component for drawing the products from within the chambers and delivering to the user's hand.

There are many different types of rays present in sunlight. The rays that are most damaging to our skin are called ultraviolet (UV) rays. UV rays are known to cause premature aging of the skin, skin cancer and other ailments such as sun burn. There are two basic types of UV rays that reach the earth's surface: UVB and UVA. UVB rays are responsible for producing sunburn. UVB rays also play a great role in causing skin cancers, including the deadly black mole form of skin cancer (i.e., malignant melanoma). UVA rays also play, in a lesser extent compared to UVB rays, a role in skin cancer formation. In addition, UVA rays penetrate more deeply into the skin and play a greater role in premature skin aging changes including wrinkle formation (i.e., photoaging).

Many commercial sunscreen products are available in the form of lotions to apply to the skin in order to block harmful rays. A sun-block product may contain organic chemicals or mineral compounds to absorb harmful rays which prevents UVA and UVB rays from causing damage to living cells.

One of the most effective known sunscreens is zinc oxide-based sunscreens, provided that it contains a sufficient concentration of zinc oxide. An effective zinc oxide-based sunscreen usually contains between 10% and 20% of zinc oxide. A drawback of zinc oxide-based sunscreens is that a layer of white color lotion remains and appears chalky on the skin. This feature makes zinc oxide-based sunscreens cosmetically unappealing, which discourages their use by consumers. Alternative sunscreens that do not have a white coloring effect contain organic chemicals that are known to block harmful rays. However, the effectiveness of such sunscreens is limited in time. The user has to re-apply the sunscreen every few hours. In addition, it has been shown that the latter chemicals can be absorbed through the skin, which raises concerns since the physiological effects of such chemicals are unknown. Furthermore, these chemicals can be hazardous to the environment.

In some zinc oxide-based sunscreens, the zinc oxide is ground up into nano sized particles. This type of sunscreen can have a high percentage of zinc oxide and be less white appearing on the skin. However, nano-sized particles are able to enter the bloodstream and be hazardous to the health of the user.

Therefore, there is a need for a product that combines a mineral based sunscreen for maximum skin protection while mitigating the cosmetic drawbacks of such products.

The present disclosure is a device and method thereof for dispensing a lotion/sunscreen product to apply to a person's skin for the benefit of protecting the skin from harmful sun rays, including UVA and UVB, while providing a cosmetically acceptable skin appearance. In one or more embodiments, the sunscreen product is comprised of a mixture of one or more compounds having property of blocking sun rays, one or more pigmented compounds for providing a color tint that matches a user's desired color, and a means for dispensing the sunscreen product with a custom color.

In the following description, specific details are set forth to provide a more thorough description of the present application. It will be apparent, however, to one skilled in the pertinent art, that the present application may be practiced without these specific details. In other instances, well known features have not been described in detail so as not to obscure the present application.

While certain sun-ray-blocking agents, such as zinc oxide, are most effective at protecting skin, the users may tend to avoid such product for unappealing cosmetic appearance of the product on the skin. Present application provides a solution the embodiment of which suits individual needs for protection from the damaging sun rays while providing a cosmetically desirable appearance.

An embodiment of the present application includes a basic sunscreen product, a pigmented product, and a delivery means for mixing the basic sunscreen product and the pigmented product into a sunscreen product. The delivery means allows a user to select a precise amount of the pigmented product to be mixed with the basic sunscreen product to obtain a sunscreen product that has a specific color, such as a desired color that matches a user's skin tone. According to some embodiments, a sunscreen product may be produced to a precise user-selected color that can be configured and modified by any user at any time.

Referring to FIG. 1, FIG. 1 is a block diagram that summarizes the concept of the invention that can embodied in one or more embodiments of the invention. Block 110 represents a basic sunscreen product. By the "basic sunscreen product" the disclosure refers to any existing sunscreen product that is suitable for use in an embodiment of the invention. For example, a basic sunscreen product, in accordance with embodiments of the invention, contains one or more sun-blocking ingredients (e.g., zinc oxide, titanium oxide etc.) mixed with other ingredients such as water and may comprise one or more moisturizing products, fragrances and any other additive for stabilizing the product's chemistry (e.g., pH buffers), preventing contamination by microorganisms or any other ingredients that may be contained in any commercially available sunscreen.

Block 120, of FIG. 1, represents a solution containing pigments for use on skin. An embodiment of the invention may use any one or more commercially available pigments for use a solution, such as a liquid, a cream or any other medium that allow the pigment to be easily mixed with the basic sunscreen product (as describe above).

Block 130, of FIG. 1, represents a means for mixing the basic sunscreen product with the pigmented solution into a sunscreen product that is ready for use and delivering the sunscreen product. The latter means may include tubes for channeling liquids/creams, pumps for moving solutions/creams through the tubes, handles for allowing a user to mechanically action the device, and any other component that is necessary to allow mixing of the appropriate sunscreen components and delivering the sunscreen product. In particular, embodiments of the invention include a dial that allows a user to select a mixture mode such that a finale sunscreen product contains a predetermined proportion of the pigmented product versus the basic sunscreen product.

As shown by block 110, a first chamber contains sun blocking active ingredients. As shown by block 120, a second chamber contains pigmented solutions. The sun blocking active ingredients of the first chamber and the pigmented solutions of the second chamber are mixed through a user-controlled mixing system, as shown by block 130. Also shown by block 130, the user-controlled mixture of the sun blocking active ingredients and the pigmented solutions are delivered to the user via a delivery device.

As shown by block 140, the final sunscreen product contains a mixture of one or more sun-blocking products mixed with the one or more pigmented solutions. The final sunscreen product has personalized proportions of the sun blocking active ingredients and pigmented solutions which are determined by the user based at least in part on the skin tone of the user to achieve the matching of a specific skin color.

Figure 2:
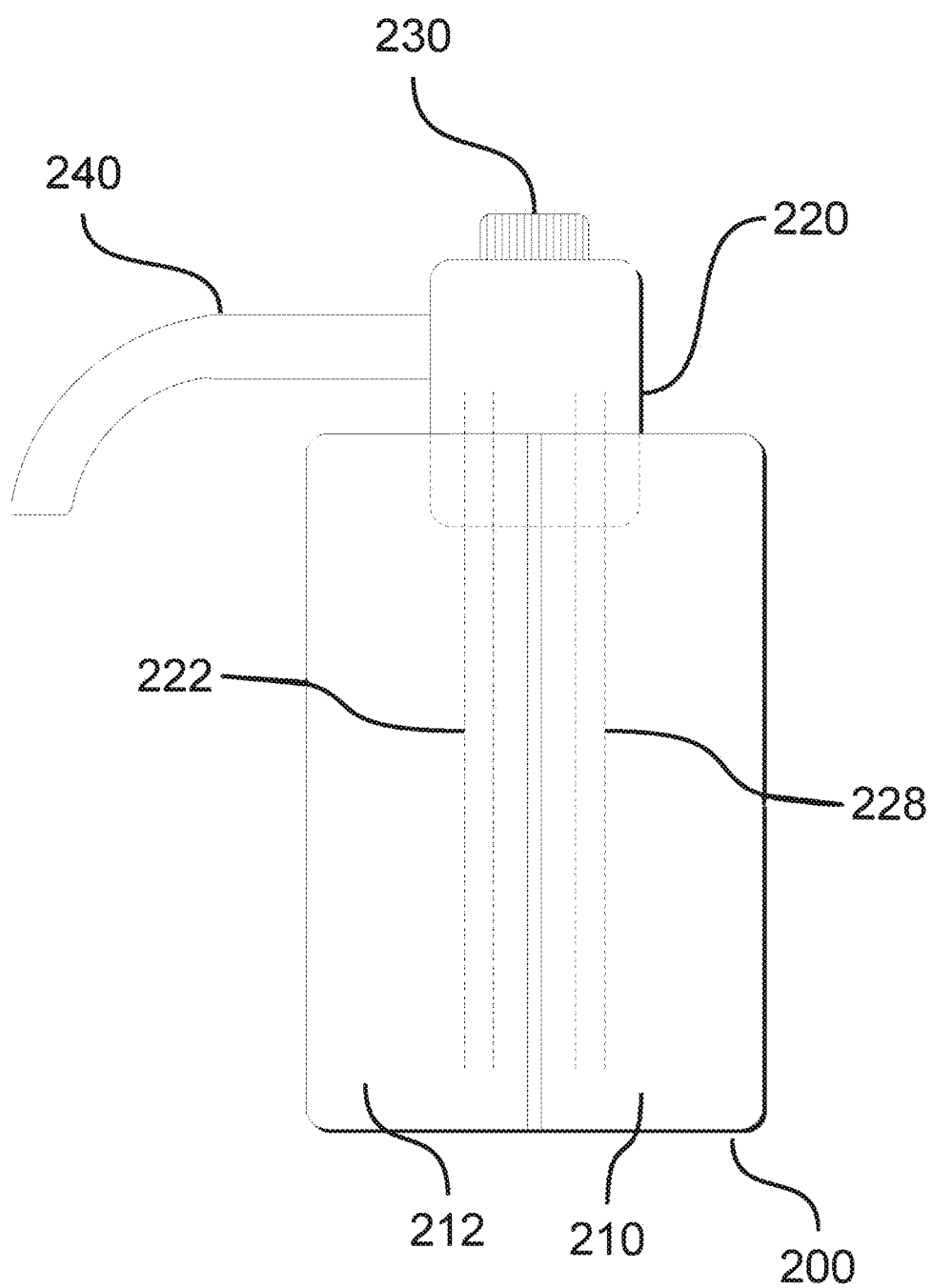
FIG. 2 illustrates a device for providing customized skin color matching sunscreen, in accordance with some embodiments.

FIG. 2 represents an implementation of the invention for delivering a customized sunscreen product the color of which is selected to match a specific skin tone. In accordance with an embodiment of the invention, a device embodying the invention includes a reservoir 200 that has two chambers 210 and 212. The first chamber 210 may include a basic sunscreen product, whereas the second chamber 212 may include on or more pigmented products. A delivery device 220 includes mechanic components (e.g., pump) to pull the basic sunscreen product and pigmented product through tubes 228 and 222 from chambers 210 and 212, respectively.

A delivery device 220 according to the invention may include a dial 230 that allows a user to select the proportion of the pigmented product versus the basic sunscreen product. In other words, dial 230 controls the intake of the product flowing through component 220. The delivery device 220 may further include a nozzle 240 to allow for the final product to be delivered to the end user.

Figure 3:
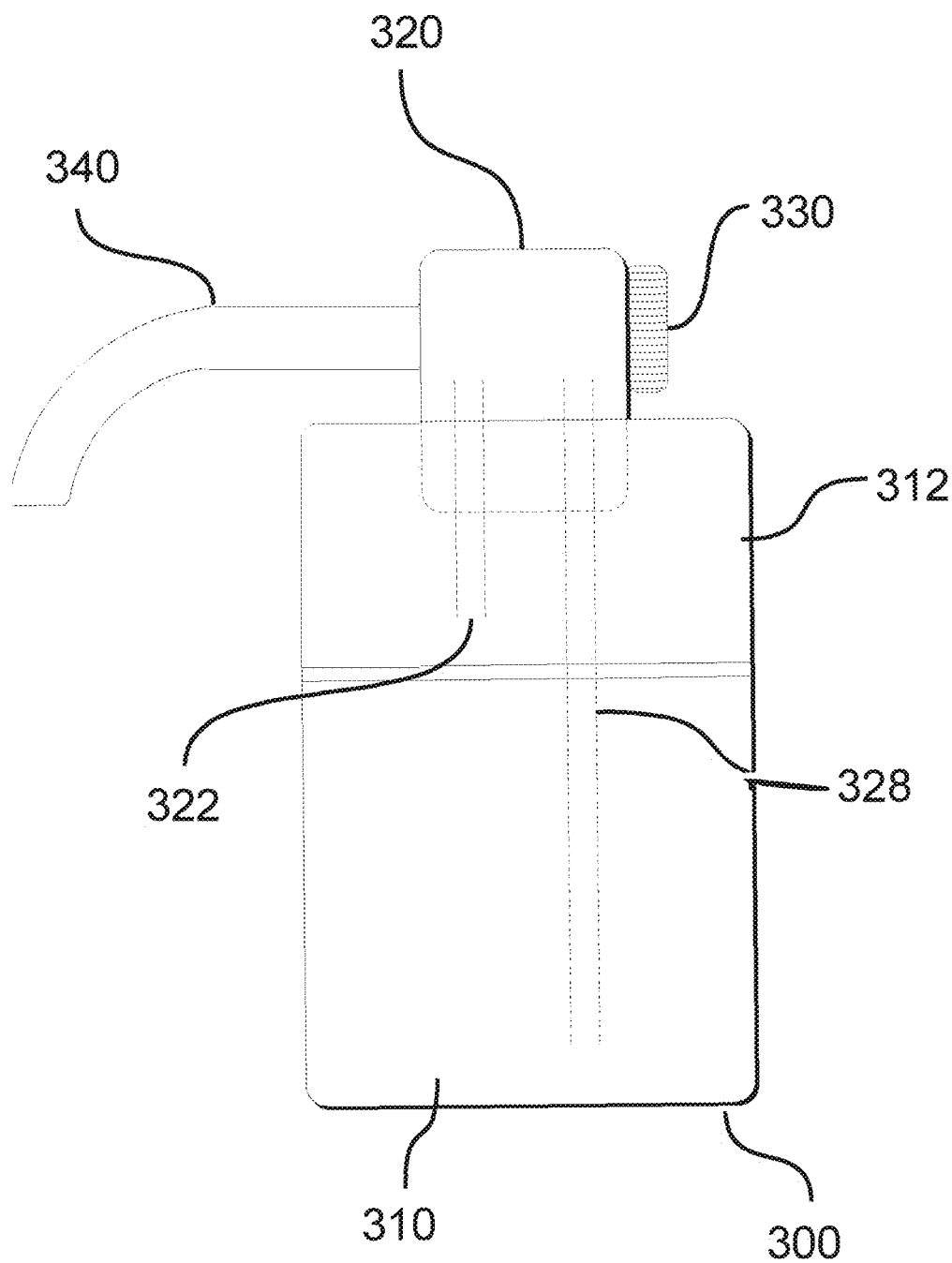
FIG. 3 illustrates a device for providing customized skin color matching sunscreen, in accordance with some embodiments.

FIG. 3 represents a different variation of the embodiment of the invention as represented in FIG. 2. In the latter example, a container 300 includes two separate chambers 310 and 312 for providing a basic sunscreen product and one or more pigmented products, respectively. Tubes, 322 and 328 allow for transferring the product to a mixing device 320 (i.e., delivery device). The proportion of the pigmented product in the final sunscreen product is determined by a dial 330. The final product is delivered through a nozzle 340. FIG. 3 illustrates an important feature in comparison to FIG. 2, in that it demonstrates that the invention may be implemented in numerous embodiments without veering off the gist of the invention.

Figure 4:
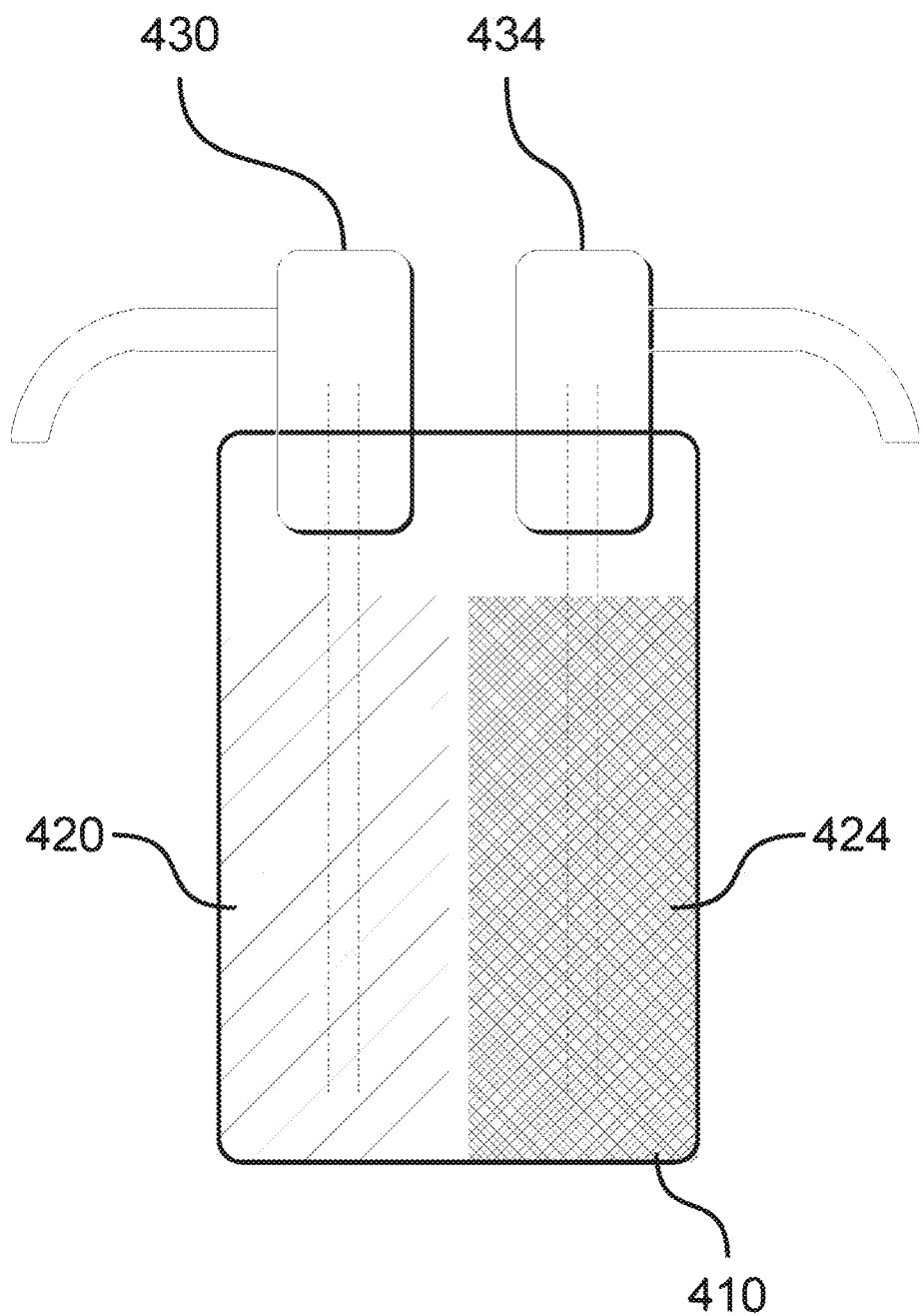
FIG. 4 illustrates a device for providing customized skin color matching sunscreen, according to some embodiments.

FIG. 4 illustrates an implementation, in accordance with the invention, that includes a dual pumping system and a dual chamber system for delivering a sunscreen product and a pigmented product. A container 410 may include a first chamber 420 for storing a mineral-based (e.g., non nano-zinc oxide) sunscreen, and a second chamber 424 for storing a cream having a dark pigment. A first pump 430 and a second pump 434 are used to deliver the sunscreen and the pigmented cream, respectively.

Thus, a device and a method are disclosed that cosmetically improve the look of the skin while giving the user the best sun protection possible. Embodiments of the invention provide a bespoke or custom dose of colored product which the user can dispense as a specific personalized dose of the tint that colors a sunscreen (e.g., zinc oxide-based sunscreen) and allows the user to match his or her own skin color.

The invention provides a highly pigmented skincare gel with a skin colored bronze/brown tint that can be individually dosed to match the skin color of the user. Use of a small amount of gel provides a light color. The more gel that is added, the darker the outcome color is when added to a white sunscreen. The more pigment is added, the darker and more saturated is the outcome. For example, when a very pale person uses the sunscreen of the invention, a very small amount of the brown coloring gel is necessary to match the light skin tone. On the opposite ends of the spectrum, someone with black skin would use a larger dose of the pigmented bronze gel over the sunscreen to match their darker skin tone. Each person regardless of their skin color will use the same product but the ratio of the two products would be customized based on their exact skin tone. Either by number of pumps if the dual chambered container has independent pumps, or by way of a "dial by ratio" dispensing container that uses a dial mechanism to change the ratio of the two components. Embodiments of the invention include various container options, it is contemplated, for ease of use, that the two products are in one container (e.g., double-chamber) and the ratio of the two components can be customized by each user.

In some embodiments, a method for providing customized skin color matching sunscreen for a user is disclosed. The method comprises: adding one or more basic sunscreen compounds, wherein the one or more sunscreen compounds comprises at least one sun blocking active agent; adding a pigmented solution to the one or more basic sunscreen compounds, wherein the pigmented solution comprises one or more pigments; determining a first amount of the one or more basic sunscreen compounds and a second amount of the pigmented solution for mixing, wherein the determining the first amount and the second amount is performed based on at least a skin tone of the user, and mechanically mixing the first amount and the second amount.

In some embodiments, at least one sun blocking active agent comprises one of: a zinc oxide, and a titanium oxide.

In some embodiments, the adding one or more basic sunscreen compounds comprises: mixing the at least one sun blocking active agent with at least one of: water, a moisturizing agent, a fragrance agent, and a stabilizing agent.

In some embodiments, the stabilizing agent acts as a pH buffer.

In some embodiments, the one or more pigments comprise at least one of: a liquid, and a cream.

In some embodiments, the first chamber and the second chamber are located vertically and next to each other.

In some embodiments, the first chamber and the second chamber are located horizontally and on top of each other.

In some embodiments, a system for providing customized skin color matching sunscreen for a user is disclosed. The system comprises a reservoir comprising: a first chamber, the first chamber configured to store one or more basic sunscreen compounds, and a second chamber, the second chamber configured to store one or more pigmented solutions, wherein the first chamber and the second chamber are separate from each other, and a delivery device located above the reservoir, the delivery device configured to pull the one or more basic sunscreen compounds from the first chamber via a first tube, and to pull the one or more pigmented solutions from the second chamber via a second tube, the delivery device comprising: a dial, the dial configured to allow selecting a first amount of the one or more basic sunscreen compounds from the first chamber and a second amount of the one or more pigmented solutions to be pulled by the delivery device from the second chamber, wherein the first amount and the second amount are determined based at least in part on a skin tone of the user, and a nozzle configured to transfer the pulled first amount of the one or more basic sunscreen compounds and second amount of the one or more pigmented solutions to the user.

In some embodiments, the one or more sunscreen compounds comprise one or more sun blocking active agents.

In some embodiments, at least one sun blocking active agent comprises one of: a zinc oxide, and a titanium oxide.

In some embodiments, at least one sun blocking active agent further comprises at least one of: water, a moisturizing agent, a fragrance agent, and a stabilizing agent.

In some embodiments, the stabilizing agent acts as a pH buffer.

In some embodiments, the one or more pigmented solutions comprise one or more pigments.

In some embodiments, the one or more pigments comprise at least one of: a liquid, and a cream.

In some embodiments, the delivery device is further configured to: prior to transferring via the nozzle, mechanically mix the pulled first amount of the one or more basic sunscreen compounds and second amount of the one or more pigmented solutions.

In some embodiments, the first chamber and the second chamber are located vertically and next to each other.

In some embodiments, a system for providing customized skin color matching sunscreen for a user is disclosed. The system comprises a reservoir comprising: a first chamber, the first chamber configured to store one or more mineral-based sunscreen compounds, and a second chamber, the second chamber configured to store one or more creams having dark pigments, wherein the first chamber and the second chamber are separate from each other; a first delivery device located on a first upper side of the reservoir, the first delivery device configured to pull the one or more mineral-based sunscreen compounds from the first chamber via a first pump and through a first tube, the first delivery device comprising: a first nozzle configured to transfer the pulled one or more mineral-based sunscreen compounds to the user, and a second delivery device located on a second upper side the reservoir, the second delivery device configured to pull the one or more creams having dark pigments from the second chamber via a second pump and through a second tube, the second delivery device comprising: a second nozzle configured to transfer the pulled one or more creams having dark pigments to the user.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best use the invention and various described embodiments with various modifications as are suited to the particular use contemplated.

What is claimed is:

1. A system for providing customized skin color matching sunscreen for a user, the system comprising:
   a reservoir comprising:
      a first chamber, the first chamber configured to store one or more basic sunscreen compounds, and
      a second chamber, the second chamber configured to store one or more pigmented solutions, wherein the first chamber and the second chamber are separate from each other, and
   a delivery device located above the reservoir, the delivery device configured to pull the one or more basic sunscreen compounds from the first chamber via a first tube, and to pull the one or more pigmented solutions from the second chamber via a second tube, the delivery device comprising:

a dial, the dial configured to allow selecting a first amount of the one or more basic sunscreen compounds from the first chamber and a second amount of the one or more pigmented solutions to be pulled by the delivery device from the second chamber, wherein the first amount and the second amount are determined based at least in part on a skin tone of the user, and a nozzle configured to transfer the pulled first amount of the one or more basic sunscreen compounds and second amount of the one or more pigmented solutions to the user.

2. The system of claim 1, wherein the one or more sunscreen compounds comprise one or more sun blocking active agents.

3. The system of claim 2, wherein at least one sun blocking active agent comprises one of: a zinc oxide, and a titanium oxide.

4. The system of claim 2, wherein at least one sun blocking active agent further comprises at least one of: water, a moisturizing agent, a fragrance agent, and a stabilizing agent.

5. The system of claim 4, wherein the stabilizing agent acts as a pH buffer.

6. The system of claim 1, wherein the one or more pigmented solutions comprise one or more pigments.

7. The system of claim 6, wherein the one or more pigments comprise at least one of: a liquid, and a cream.

8. The system of claim 1, wherein the delivery device is further configured to:
prior to transferring via the nozzle, mechanically mix the pulled first amount of the one or more basic sunscreen compounds and second amount of the one or more pigmented solutions.

9. The system of claim 1, wherein the first chamber and the second chamber are located vertically and next to each other.

10. The system of claim 1, wherein the first chamber and the second chamber are located horizontally and on top of each other.

11. A system for providing customized skin color matching sunscreen for a user, the system comprising:
a reservoir comprising:
a first chamber, the first chamber configured to store one or more mineral-based sunscreen compounds, and
a second chamber, the second chamber configured to store one or more creams having dark pigments, wherein the first chamber and the second chamber are separate from each other;
a first delivery device located on a first upper side of the reservoir, the first delivery device configured to pull the one or more mineral-based sunscreen compounds from the first chamber via a first pump and through a first tube, the first delivery device comprising:
a first nozzle configured to transfer the pulled one or more mineral-based sunscreen compounds to the user, and
a second delivery device located on a second upper side the reservoir, the second delivery device configured to pull the one or more creams having dark pigments from the second chamber via a second pump and through a second tube, the second delivery device comprising:
a second nozzle configured to transfer the pulled one or more creams having dark pigments to the user.

12. The system of claim 11, wherein the first chamber and the second chamber are located vertically and next to each other.

13. The system of claim 11, wherein the first nozzle and the second nozzle can be depressed independently of one another.

14. The system of claim 11, wherein the amount of mineral-based sunscreen transferred from the first nozzle is determined by the user based upon a preselected amount indicated on the reservoir, and wherein the amount of one or more creams having dark pigments transferred from the second nozzle is determined by the user based upon a preselected amount indicated on the reservoir.

15. A system for providing customized skin color sunscreen, the system comprising:
a reservoir comprising:
a first chamber, the first chamber configured to store one or more basic sunscreen compounds, and
a second chamber, the second chamber configured to store one or more pigmented solutions, wherein the first chamber and the second chamber are separate from each other, and
a delivery device located above the reservoir, the delivery device configured to pull the one or more basic sunscreen compounds from the first chamber via a first tube, and to pull the one or more pigmented solutions from the second chamber via a second tube, the delivery device comprising:
a dial by ratio delivery device, the dial configured to allow selecting a first amount of the one or more basic sunscreen compounds to be pulled by the delivery device from the first chamber according to the ratio selected on the dial by the user, and a second amount of the one or more pigmented solutions to be pulled by the delivery device from the second chamber according to the ratio on the dial selected by the user, wherein the first amount and the second amount are determined based upon the desired skin tone selected by the user and indicated on the dial, and
a nozzle configured to transfer the pulled first amount of the one or more basic sunscreen compounds and second amount of the one or more pigmented solutions to the user.

16. The system of claim 15, wherein prior to transferring the first amount of the one or more basic sunscreen compounds and the second amount of the one or more pigmented solutions, the first amount and second amount are mechanically mixed to dispense from the nozzle in a single, skin colored desired solution.

17. The system of claim 15, wherein the one or more sunscreen compounds comprise one or more sun blocking active agents.

18. The system of claim 17, wherein at least one sun blocking active agent further comprises at least one of: zinc oxide, a titanium oxide, water, a moisturizing agent, a fragrance agent, and a stabilizing agent.

19. The system of claim 15, wherein the dial is a selection indicator to select the first amount of the one or more basic sunscreen compounds and the second amount of the one or more pigmented solutions.

20. The system of claim 15, wherein the first chamber and second chamber are refillable.

* * * * *